(12) United States Patent
Miwa et al.

(10) Patent No.: US 7,776,579 B2
(45) Date of Patent: Aug. 17, 2010

(54) METHOD OF DEGRADING HARDLY DEGRADABLE PROTEIN

(75) Inventors: Takehiro Miwa, Kanagawa (JP); Koji Nishizawa, Saitama (JP); Yoshie Hayashi, Saitama (JP); Manabu Watanabe, Kanagawa (JP); Yuichi Murayama, Ibaraki (JP); Miyako Yoshioka, Ibaraki (JP); Katsuhiro Miura, Ibaraki (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 513 days.

(21) Appl. No.: 10/532,605

(22) PCT Filed: Oct. 24, 2003

(86) PCT No.: PCT/JP03/13658

§ 371 (c)(1),
(2), (4) Date: Aug. 18, 2005

(87) PCT Pub. No.: WO2004/042049

PCT Pub. Date: May 21, 2004

(65) Prior Publication Data

US 2006/0134092 A1    Jun. 22, 2006

(30) Foreign Application Priority Data

Oct. 24, 2002    (JP) .............................. 2002-309248

(51) Int. Cl.
*C12N 9/56* (2006.01)

(52) U.S. Cl. ........................ 435/222; 435/183; 435/212

(58) Field of Classification Search ........................ None
See application file for complete search history.

(56) References Cited

U.S. PATENT DOCUMENTS 5,981,255 A    11/1999    Miyota et al.
6,613,505 B2    9/2003    Shih

FOREIGN PATENT DOCUMENTS

| CN | 1201489 | 12/1998 |
|---|---|---|
| JP | 6-46871 | 2/1994 |
| JP | 10-500863 | 1/1998 |
| WO | WO 95/33056 | 12/1995 |
| WO | WO 98/20115 A1 | 5/1998 |
| WO | WO 98/30682 A1 * | 7/1998 |
| WO | WO 02/053723 A2 | 7/2002 |
| WO | WO 02/083082 A1 | 10/2002 |

OTHER PUBLICATIONS

Genov et al., Biochem J, 1982, vol. 207, p. 193-200.*
Lin et al, "Nucleotide Sequence and Expression of Kera, the Gene Encoding a Keartinolytic Protease of Bacillus licheniformis PWD-1", Applied and Environmental Microbiology, Washington, D.C., US, vol. 61, No. 4, Apr. 1995, pp. 1469-1474, XP002042752.
Yoshioka et al, "Characterization of a Proteolytic Enzyme Derived From a Bacillus Strain That Effectively Degrades Prion Protein", Journal of Applied Microbiology Feb. 2007, vol. 102, No. Feb. 2007, pp. 509-515, XP002422549.
Lin et al., App. Env. Microbiol. 1992, vol. 58, No. 10, pp. 3271-3275.
Nature, Aug. 11, 1994, pp. 471-474, vol. 370.

* cited by examiner

*Primary Examiner*—L Blaine Lankford
*Assistant Examiner*—Kade Ariani
(74) *Attorney, Agent, or Firm*—Sughrue Mion, PLLC

(57) ABSTRACT

Disclosed is an agent for digesting a protein highly resistant to denaturation and degradation, comprising as an active ingredient an enzyme exhibiting an activity of digesting a protein highly resistant to denaturation and degradation and having the following properties:
(a) activity and substrate specificity: hydrolyzing a peptide bond of a protein highly resistant to denaturation and degradation;
(b) molecular weight: 31,000 (determined by SDS-polyacrylamide gel electrophoresis using a homogeneous gel having a gel concentration of 12%);
(c) isoelectric point: pI 9.3 (determined by polyacrylamide gel isoelectric focusing electrophoresis);
(d) optimum pH: pH 9.0 to 10.0; and
(e) optimum temperature for activity: 60 to 70° C.

8 Claims, 6 Drawing Sheets

F I G. 8
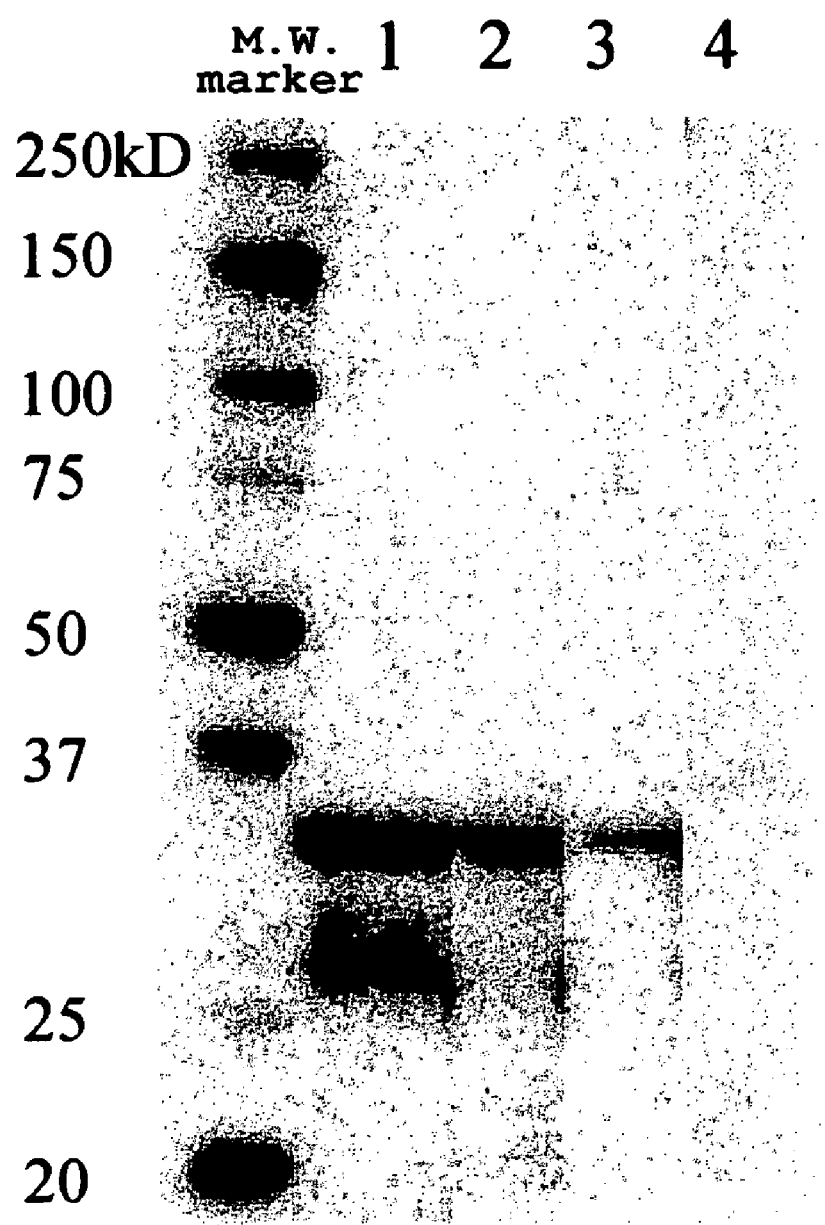

METHOD OF DEGRADING HARDLY DEGRADABLE PROTEIN

TECHNICAL FIELD

The present invention relates to an agent for digesting a protein highly resistant to denaturation and degradation (particularly a pathogenic prion protein) and a method for digesting the protein.

Background Art

A pathogenic prion protein seems to be involved in such diseases as scrapie in sheep or mice, Creutzfeldt-Jakob disease (CJD) in humans, and bovine spongiform encephalopathy (BSE; popularly known as mad cow disease) in cattle give rise to nervous symptoms such as dysstasia or dysbasia. It is noted that human consumption of beef infected with the pathogenic prion protein may cause a variant Creutzfeldt-Jakob disease (vCJD) by infection. In particular, BSE is an extremely serious disease in the light of a safe supply of beef for human consumption.

Such diseases may develop when the pathogenic prion protein transferred into the human body from the outside causes a conformational change of a normal prion protein generally located in the brain [Nature, (Great Britain), 1994, Vol. 370, p. 471 (non-patent reference 1)]. To prevent the development of disease by an infection of the pathogenic prion protein, it is necessary to digest and detoxify the pathogenic prion protein as a cause thereof to the extent that the disease does not develop.

However, the pathogenic prion protein is believed to be extremely stable when subjected to a commonly used sterilizing treatment (such as boiling) and exhibits little or no loss of infectivity by the sterilizing treatment. Further, although the pathogen is a protein, it is not difficult to digest the pathogen completely with a conventional protease. Under these circumstances, a method for digesting the pathogenic prion protein efficiently and a method for preventing the diseases from developing by infection are desired.

As a method for digesting a protein highly resistant to denaturation and degradation such as a pathogenic prion protein, for example, Japanese Unexamined Patent Publication (Kokai) No. 6-46871 (patent reference 1) discloses a method for digesting keratin-containing proteins highly resistant to conventional proteases, using keratinase, a protease, derived from *Bacillus licheniformis* PWD-1. The publication discloses that keratinase is used in digesting keratin-containing proteins (for example, animal hair, human hair, or feathers), but neither discloses nor suggests any effects of the keratinase on a pathogenic prion protein.

In this connection, a DNA encoding the keratinase derived from *Bacillus licheniformis* PWD-1 was obtained [Unexamined International Publication (Kohyo) No. 10-500863 (patent reference 2)].

Further, U.S. Pat. No. 6,613,505 (patent reference 3) discloses that the keratinase derived from *Bacillus licheniformis* PWD-1 is used in digesting a pathogenic prion protein highly resistant to denaturation and degradation. However, to reduce or digest the pathogenic prion protein by the method disclosed in U.S. Pat. No. 6,613,505, two of treatment step, that is, a heat treatment as a pretreatment, and an enzyme treatment, are necessary. In this method, an apparatus for heating is necessary, and thus it is not easy to carry out the method in common facilities without such an apparatus for heating. Further, the two-step procedures are complicated.

Furthermore, International Publication No. 02/053723 (patent reference 4) discloses that a heat-resistant protease is used in digesting a pathogenic prion protein. However, it discloses that when a pathogenic prion protein was digested by a protease derived from *Bacillus thermoproteolytics* Rokko described in Examples thereof, the pathogenic prion protein was not sufficiently digested with the protease alone, but was sufficiently digested with the protease in the presence of sodium dodecyl sulfate. In addition, a neutral salt is necessary to activate the protease. Further, the protease requires a metal ion, and thus when a chelating agent is present in a reaction, the activity is remarkably decreased.

(non-patent reference 1) Nature, (Great Britain), 1994, Vol. 370, p. 471
(patent reference 1) Japanese Unexamined Patent Publication (Kokai) No. 6-46871
(patent reference 2) Unexamined International Publication (Kohyo) No. 10-500863
(patent reference 3) U.S. Pat. No. 6,613,505
(patent reference 4) International Publication No. 02/053723

DISCLOSURE OF THE INVENTION

An object of the present invention is to provide an enzyme produced at a low cost and exhibiting a high activity of digesting a protein highly resistant to denaturation and degradation (particularly a pathogenic prion protein) in comparison with known proteases; an agent for digesting a protein highly resistant to denaturation and degradation and an agent for detoxifying a pathogenic prion protein, containing the enzyme as an active ingredient; and a method for digesting a protein highly resistant to denaturation and degradation (particularly a pathogenic prion protein) and a method for detoxifying a pathogenic prion protein, using the enzyme or the agent.

The present inventors found an enzyme exhibiting an extremely high activity of digesting a protein strongly resistant to denaturation and degradation (particularly a pathogenic prion protein) derived from a microorganism belonging to genus *Bacillus*, in comparison with enzymes known to digest a protein highly resistant to denaturation and degradation.

The enzyme which may be used in the present invention exhibited excellent properties, as shown in Examples described below, in comparison with the above-mentioned enzymes previously reported to be used in digesting a pathogenic prion protein, for example, the enzyme (keratinase) prepared from *Bacillus licheniformis* PWD-1 disclosed in U.S. Pat. No. 6,613,505, and the enzyme prepared from *Bacillus thermoproteolyticus* Rokko disclosed in International Publication No. 02/053723.

Particularly, it was found that the enzyme which may be used in the present invention exhibited an extremely high activity of digesting a pathogenic prion protein in comparison with the enzyme prepared from *Bacillus licheniformis* PWD-1 (see Examples 7 and 8). Further, it was surprisingly found that the protein was digested without a thermal treatment described in U.S. Pat. No. 6,613,505 (see Examples 7 and 8).

In comparison with the enzyme prepared from *Bacillus thermoproteolyticus* Rokko, it was found that the enzyme which may be used in the present invention exhibited an extremely high activity of digesting a pathogenic prion protein (see Examples 9 to 11). Further, it was surprisingly found that the protein exhibited an excellent activity of digesting a pathogenic prion protein regardless of the presence of sodium dodecyl sulfate (see Examples 9 to 11).

Further, the present inventors provided an agent for digesting a protein highly resistant to denaturation and degradation and an agent for detoxifying a pathogenic prion protein, containing the newly found enzyme as an active ingredient, and further found a method for digesting a protein highly resistant to denaturation and degradation (particularly a pathogenic prion protein) and a method for detoxifying a pathogenic prion protein, using the enzyme or the agent.

The present invention relates to:

[1] an agent for digesting a protein highly resistant to denaturation and degradation, comprising as an active ingredient an enzyme exhibiting an activity of digesting a protein highly resistant to denaturation and degradation and having the following properties:
(a) activity and substrate specificity: hydrolyzing a peptide bond of a protein highly resistant to denaturation and degradation,
(b) molecular weight: 31,000 (determined by an SDS-polyacrylamide gel electrophoresis using a homogeneous gel having a gel concentration of 12%),
(c) isoelectric point: pI 9.3 (determined by polyacrylamide gel isoelectric focusing electrophoresis),
(d) optimum pH: pH 9.0 to 10.0, and
(e) optimum temperature for activity: 60 to 70° C.;

[2] the agent of [1], wherein the enzyme has the following property:
(g) exhibiting an activity of 2 U/g or more as the activity of digesting a protein highly resistant to denaturation and degradation (determined as an activity of digesting keratin azure;

[3] the agent of [1] or [2], wherein the enzyme has the following property:
(h) derived from a microorganism belonging to genus *Bacillus*;

[4] an agent for digesting a protein highly resistant to denaturation and degradation, comprising as an active ingredient an enzyme selected from the group consisting of
(X) an enzyme comprising the amino acid sequence of SEQ ID NO: 2;
(Y) a modified enzyme exhibiting an activity of digesting a protein highly resistant to denaturation and degradation, and comprising an amino acid sequence in which one or plural amino acids are deleted, substituted, or added in the amino acid sequence of SEQ ID NO: 2; and
(Z) a homologous enzyme exhibiting an activity of digesting a protein highly resistant to denaturation and degradation, and comprising an amino acid sequence having an 85% or more homology with the amino acid sequence of SEQ ID NO: 2;

[5] the agent of [1] to [4], wherein the protein highly resistant to denaturation and degradation is a pathogenic prion protein;

[6] a method for digesting a protein highly resistant to denaturation and degradation, comprising the step of bringing the protein highly resistant to denaturation and degradation into contact with the agent or enzyme of [1] to [5];

[7] use of the enzyme of [1] to [5], in the manufacture of an agent for digesting a protein highly resistant to denaturation and degradation;

[8] an agent for detoxifying a pathogenic prion protein in a subject which may be contaminated with a pathogenic prion protein, comprising as an active ingredient the enzyme of [1] to [5];

[9] a method for detoxifying a pathogenic prion protein, comprising the step of bringing a subject which may be contaminated with a pathogenic prion protein into contact with the enzyme of [1] to [5] or the agent of [8];

[10] a method for detoxifying a pathogenic prion protein, comprising the step of bringing a subject which may be contaminated with a pathogenic prion protein into contact with the enzyme of [1] to [5] or the agent of [8], without preheating the subject;

[11] a method for detoxifying a pathogenic prion protein, comprising the step of bringing a subject which may be contaminated with a pathogenic prion protein into contact with the enzyme of [1] to [5] or the agent of [8], without preheating the subject at 90° C. or more; and

[12] use of the enzyme of [1] to [5], in the manufacture of an agent for detoxifying a pathogenic prion protein.

BRIEF DESCRIPTION OF DRAWINGS

FIG. 8 shows the results in which the hamster pathogenic prion protein (strain Sc237) was digested in the presence of SDS with enzyme composition A' used in the present invention or thermoase for comparison.

BEST MODE FOR CARRYING OUT THE INVENTION

Figure 1:
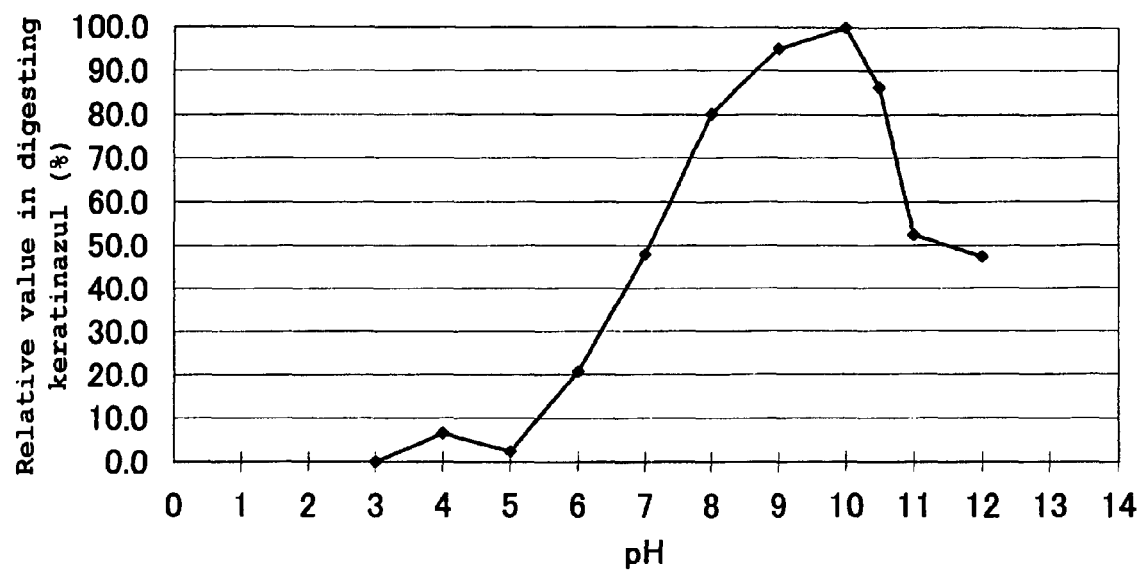
FIG. 1 is a graph showing the optimum pH and stable pH of a purified enzyme used in the present invention at 37° C.

The present invention will be explained in detail hereinafter.

The enzyme used in the present invention exhibits an activity of digesting a protein highly resistant to denaturation and degradation, that is, a hydrolytic activity of peptide bonds in the protein highly resistant to denaturation and degradation.

The term "protein highly resistant to denaturation and degradation" as used herein means a protein which is not easily digested with a commonly used protease such as proteinase K or trypsin. More particularly, it means a protein which is not completely digested when treated with 1 µg/mL of proteinase K at 37° C. for 1 hour. As the protein highly resistant to denaturation and degradation, there may be mentioned, for example, a pathogenic prion protein, keratin, collagen, or elastin.

The term "pathogenic prion protein" as used herein means a protein which is involved in the onset of, for example, scrapie, CJD, or BSE, more particularly, a prion protein conformationally changed from a normal prion generally located in the brain. The pathogenic prion protein includes a protein derived from, for example, a human, hamster, mouse, bovine, or sheep.

The normal prion protein and the pathogenic prion protein have the same amino acid sequence, but different tertial structures. In the normal prion protein, the content of the α-helix structure in which the polypeptide chain of the prion protein takes a spiral form is high, and the content of the β-sheet structure in which the polypeptide chain takes a plane form is low. In construct, the pathogenic prion protein contains a high content of the β-sheet structure (Pan, PNAS, 90, 10962, 1993). In addition, each prion protein derived from the above animals has a high homology among the amino acid sequences thereof, and shows the same property in which a conformational change of the normal prion protein causes the change to the pathogenic prion protein highly resistant to denaturation and degradation.

The pathogenic prion protein considered to be a pathogen of the above diseases is extremely stable when subjected to a general sterilizing treatment such as boiling, and thus exhibits little or no loss of infectivity by such a sterilizing treatment. Further, while the normal prion protein is easily digested, and thus a half life thereof in the body is approximately 2 hours, the pathogenic prion protein has a half life of 24 hours or more, and is highly resistant to digestion. When the digestibilities of the normal and pathogenic prion proteins to conventional proteases such as commercially available proteinase K were evaluated, it was reported that the normal prion protein was easily digested and was sensitive, but the pathogenic prion protein exhibited a low digestibility and was highly resistant to digestion (Prusiner, Science, 252, 1515, 1991). It is considered that the difference in digestibility is due to the difference in the tertial structures as described above.

The normal prion protein may be distinguished from the pathogenic prion protein, for example, by utilizing the difference in digestibility to a protease. For example, a tissue derived from an animal which may be contaminated with the pathogenic prion protein is homogenized to prepare a homogeneous suspension. The suspension is treated with a commonly used protease such as proteinase K, and analyzed by Western blotting (Burnette, Anal. Biochem., 112, 195, 1981) to detect the prion protein. When no band is detected, it may be judged that the tissue contains only the normal prion protein. When a protein band resistant to the protease is detected, it may be judged that the tissue contains the pathogenic prion protein.

The term "activity of digesting a protein highly resistant to denaturation and degradation" as used herein means a hydrolytic activity of peptide bonds in the protein highly resistant to denaturation and degradation. As a unit of the "activity of digesting a protein highly resistant to denaturation and degradation", two different units are used herein. In the first unit, "1 unit" of an enzyme is defined as an amount of the enzyme which can generate a product corresponding to 1 µmol of glycine per minute, when a suspension containing 0.5% (as a final concentration) of keratin powder (derived from human hair; Nacalai Tesque) is treated with the enzyme at pH 8.0 and 60° C. for 1 hour. In the second unit, "1 unit" of an enzyme is defined as 0.001 of an amount of absorbance changed, when a suspension containing 0.8% (as a final concentration) of keratin azure (Sigma) is treated with the enzyme at pH 8.0 and 37° C. for 16 hours, and an amount of a pigment released to a supernatant of the reaction mixture per minute is measured at an absorbance of 595 nm.

In this connection, the keratin azure is a compound in which an azo pigment is bound to keratin (for example, keratin derived from wool). The keratin azure is widely used as a substance for measuring an activity (i.e., a keratinase activity) of digesting keratin, a protein highly resistant to denaturation and degradation, because an azo-pigment-bound amino acid or an azo-pigment-bound peptide released by digesting peptide bonds in keratin can be spectroscopically measured.

The "activity of digesting a pathogenic prion protein" as used herein means a hydrolytic activity of peptide bonds in the pathogenic prion protein. A degree or strength of the "activity of digesting a pathogenic prion protein" may be judged, for example, by analyzing a digestion of the pathogenic prion protein contained in a suspension containing 1% of a brain tissue derived from a mouse suffering from scrapie.

More particularly, a brain tissue derived from a mouse infected with the pathogenic prion protein is homogenized to prepare a homogeneous suspension, and the suspension is treated with an enzyme or enzyme composition to be judged. Proteins contained in the reaction mixture are separated by electrophoresis, and the prion protein is detected by Western blotting. When no band is detected, the result shows that the enzyme or enzyme composition to be judged exhibits an extremely high activity of digesting a pathogenic prion protein. When a protein band resistant to the protease is detected and the band is thin, the result shows that the enzyme or enzyme composition exhibits a moderate activity of digesting a pathogenic prion protein. When the protein band is dense, the result shows that the enzyme or enzyme composition exhibits a low activity of digesting a pathogenic prion protein.

Protein Exhibiting an Activity of Digesting a Protein Highly Resistant to Denaturation and Degradation (Particularly a Pathogenic Prion Protein)

In the present invention, for example, an enzyme having the following properties may be used.

(a) Activity and Substrate Specificity

The enzyme hydrolyzes one or more peptide bonds of a protein, particularly one or more peptide bonds of a protein highly resistant to denaturation and degradation (such as a pathogenic prion protein). As to the substrate specificity, the enzyme exhibits high activities of digesting casein, collagen, elastin, and keratin, as well as the pathogenic prion protein.

(b) Molecular Weight

The molecular weight determined by an SDS-polyacrylamide gel electrophoresis using a 12% homogeneous gel (i.e., a homogeneous gel in which a concentration of polyacrylamide is 12%) is approximately 31,000.

The molecular weight determined by an SDS-polyacrylamide gel electrophoresis using a 15% homogeneous gel (i.e., a homogeneous gel in which a concentration of polyacrylamide is 15%; such as a gel manufactured by ATTO) is approximately 26,000.

(c) Isoelectric Point

The isoelectric point (pI) determined by a polyacrylamide gel isoelectric focusing electrophoresis is approximately 9.3.

(d) Optimum pH and Stable pH

The optimum pH, evaluated by an activity of digesting keratinazure as an index, is approximately pH 9.0 to 10.0. The enzyme exhibits a stable activity at approximately pH 7.0 to 12.0, and a high activity at approximately pH 8.0 to 10.5.

(e) Optimum Temperature for Activity

The optimum temperature for activity, evaluated by an activity of digesting keratin azure as an index, is approximately 60 to 70° C.

(f) Deactivating pH

The enzyme was inactivated at approximately pH 5 or less, when evaluated by an activity of digesting keratinazure as an index.

In Table 1, the above properties of the enzyme which may be used in the present invention are shown in comparison with those of a known protease exhibiting an activity of digesting a protein highly resistant to denaturation and degradation (keratinase derived from *Bacillus licheniformis* PWD-1).

TABLE 1

| | Enzyme used in the present invention | Known protease |
|---|---|---|
| Activity and substrate specificity | | |
| pathogenic prion protein | ++ | + |
| casein | + | + |
| collagen | + | + |
| elastin | + | + |
| keratin | + | + |
| Molecular weight | 31,000 | 33,000 |
| Isoelectric point | 9.3 | 7.25 |
| Optimum pH | 9.0 to 10.0 | 7.5 |
| Optimum temperature | 60 to 70° C. | 50° C. |

In another embodiment of the present invention, an enzyme comprising the amino acid sequence of SEQ ID NO: 2, or a modified or homologous enzyme thereof may be used.

The "enzyme comprising the amino acid sequence of SEQ ID NO: 2" includes, for example, an enzyme consisting of the amino acid sequence of SEQ ID NO: 2;

a fusion enzyme consisting of an amino acid sequence in which an appropriate marker sequence is added to the N-terminus and/or the C-terminus of the polypeptide consisting of the amino acid sequence of SEQ ID NO: 2, and exhibiting an activity of digesting a protein highly resistant to denaturation and degradation (particularly a pathogenic prion protein);

a fusion enzyme consisting of the polypeptide consisting of the amino acid sequence of SEQ ID NO: 2 and a partner for fusion, and exhibiting an activity of digesting a protein highly resistant to denaturation and degradation (particularly a pathogenic prion protein); and an enzyme consisting of an amino acid sequence in which a presequence (signal sequence) or a fragment thereof is added to the N-terminus of the amino acid sequence of SEQ ID NO: 2. In addition, a fusion enzyme consisting of an amino acid sequence in which an appropriate marker sequence and/or an appropriate partner for fusion is further added to the amino acid sequence in which a presequence is added to the N-terminus of the amino acid sequence of SEQ ID NO: 2, is included in the "enzyme comprising the amino acid sequence of SEQ ID NO: 2".

As the presequence, a naturally-occurring presequence or an artificially designed sequence may be used. As the naturally-occurring presequence, not only a presequence derived from *Bacillus licheniformis* (particularly a presequence of a *Bacillus licheniformis* derived enzyme capable of digesting a protein highly resistant to denaturation and degradation), but also a presequence derived from organisms other than *Bacillus licheniformis*, may be used.

As the marker sequence, for example, a sequence for easily carrying out a confirmation of polypeptide expression, a confirmation of intracellular localization thereof, or a purification thereof may be used. As the sequence, there may be mentioned, for example, a FLAG tag, a hexa-histidine tag, a hemagglutinin tag, or a myc epitope.

As the partner for fusion, there may be mentioned, for example, a polypeptide for purification [for example, glutathione S-transferase (GST) or a fragment thereof], a polypeptide for detection [for example, hemagglutinin or β-galactosidase αpeptide (LacZ α), or a fragment thereof], or a polypeptide for expression (for example, a signal sequence).

In the above fusion polypeptide, an amino acid sequence which can be specifically digested with a protease such as thrombin or factor Xa may be optionally inserted between the polypeptide consisting of the amino acid sequence of SEQ ID NO: 2 and the marker sequence or the partner for fusion.

The term "modified enzyme" as used herein means a protein comprising an amino acid sequence in which one or plural (for example, one or several) amino acids are deleted, substituted, or added in the amino acid sequence of SEQ ID NO: 2, and exhibiting an activity of digesting a protein highly resistant to denaturation and degradation (particularly a pathogenic prion protein). In this connection, the number of amino acids to be modified, such as "deleted, substituted, or added", is preferably 1 to 30, more preferably 1 to 10, most preferably 1 to 6.

The "modified enzyme" includes a protein comprising an amino acid sequence in which one or plural (for example, one or several) amino acids are conservatively substituted in the amino acid sequence of SEQ ID NO: 2, and exhibiting an activity of digesting a protein highly resistant to denaturation and degradation (particularly a pathogenic prion protein). The term "conservative substitution" as used herein means that one or plural amino acid residues contained in a protein are replaced with different amino acids having similar chemical properties so that the activities of the protein are not substantially changed. As the conservative substitution, there may be mentioned, for example, a substitution of a hydrophobic residue for another hydrophobic residue, or a substitution of a polar residue for another polar residue having the same charge. Amino acids which have similar chemical properties and can be conservatively substituted with each other are known to those skilled in the art.

More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine. As acidic amino acids having a negative charge, there may be mentioned, for example, aspartic acid or glutamic acid.

The term "homologous protein" as used herein means a protein comprising an amino acid sequence having an 85% or more (preferably 90% or more, more preferably 95% or more, still further preferably 98% or more, most preferably 99% or more) homology with the amino acid sequence of SEQ ID NO: 2, and exhibiting an activity of digesting a protein highly resistant to denaturation and degradation (particularly a pathogenic prion protein). The term "homology" as used herein means a value obtained by a known program for a homology search, BLAST (Basic local alignment search tool; Altschul, S. F. et al., J. Mol. Biol., 215, 403-410, 1990; obtained from National Center for Biotechnology Information).

The enzyme comprising the amino acid sequence of SEQ ID NO: 2, or the modified or homologous enzyme thereof exhibits an activity of digesting a protein highly resistant to denaturation and degradation (particularly a pathogenic prion protein) of preferably 2 U/g or more, more preferably 2 to 500 U/g, still further preferably 10 to 500 U/g, most preferably 20 to 500 U/g, as an activity of digesting keratin azure. When an activity of digesting keratin powder is used as an index, it is preferably 1 U/g or more, more preferably 1 to 5000 U/g, most preferably 5 to 3000 U/g.

An origin of the enzyme used in the present invention is not particularly limited, so long as it is an enzyme having the above-mentioned physical and chemical properties, an enzyme comprising the amino acid sequence of SEQ ID NO: 2, or a modified or homologous enzyme thereof. For example, enzymes derived from animals, plants, or microorganisms may be used. An enzyme produced by an microorganism belonging to genus *Bacillus* is preferable, an enzyme produced by *Bacillus licheniformis* is more preferable, and an enzyme produced by *Bacillus licheniformis* MSK-103 (FERM BP-08487) is most preferable. Further, a mutant derived from the microorganisms may be used.

Deposit of Microorganism

*Bacillus licheniformis* MSK-103 (FERM BP-08487) was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 16, 2002, and was transferred to an international deposit on Sep. 16, 2003. The international deposit number (a number in parenthesis [ ] following the international deposit number is a domestic deposit number) is FERM BP-08487 [FERM P-19068].

As the enzyme used in the present invention, subtilisins may be used, and subtilisin DY (WO98/30682) is preferable.

The enzyme used in the present invention may be obtained by isolating and purifying the enzyme of interest from a microorganism, for example, as described in Example 1. Alternatively, it may be obtained by expressing a polynucleotide encoding the protein of interest in an appropriate host by genetic engineering techniques, and isolating and purifying the produced protein, as described below.

To obtain the enzyme used in the present invention from a microorganism producing the enzyme, the microorganism may be cultivated under the conditions suitable for the microorganism, and the obtained broth, supernatant, or microorganism may be treated by known separation and purification techniques. Hereinafter procedures of the microorganism cultivation and the protein purification will be explained in accordance with an embodiment using *Bacillus licheniformis* MSK-103 (FERM BP-08487) as the microorganism producing the enzyme used in the present invention.

A culture medium [1% polypeptone, 0.2% yeast extract, and 0.1% magnesium sulfate heptahydrate (pH 7.0)] is autoclaved by a conventional method, and the medium is inoculated with *Bacillus licheniformis* MSK-103 (FERM BP-08487). A cultivation is carried out at 37-50° C. under aeration and agitation for 24-72 hours. The resulting broth is centrifuged at approximately 3000 G to obtain a supernatant containing the enzyme used in the present invention. If necessary, the supernatant is concentrated 2 to 50-fold with an ultrafilter (5,000 to 30,000-molecular-weight cutoff) to obtain a concentrated supernatant containing the enzyme used in the present invention.

The above supernatant or the above concentrated supernatant contains various substances other than the enzyme used in the present invention, and thus the enzyme used in the present invention may be further purified, for example, by the following procedures.

The above supernatant or concentrated supernatant is filtered with a microfilter membrane (pore size=approximately 0.45 μm) to remove microorganisms. Ammonium sulfate is added to the resulting sterile filtrate, to a final concentration of 1 mol/L, and a buffer agent (Tris-HCl) is further added to pH 8.5 and a final concentration of 50 mmol/L. For a further purification by a hydrophobic chromatography, the prepared solution is adsorbed to a phenyl Sepharose column, and eluted by a linear gradient with ammonium sulfate (1 mol/L to 0 mol/L) in a Tris-HCl buffer, to obtain a fraction containing the enzyme used in the present invention. The fraction is concentrated 20 to 30-fold with an ultrafilter (5,000 to 10,000-molecular-weight cutoff), and a gel filtration chromatography is carried out, for example, using Superdex 75 (Pharmacia) gel. The concentrated solution is developed through the gel with a phosphate buffer (0.025 mol/L, pH 7.0) containing 0.1 mol/L sodium chloride as an eluent, to obtain the enzyme used in the present invention. According to the above purification procedures, the enzyme used in the present invention can be purified as a band by an electrophoretic analysis.

Polynucleotide Encoding Protein having an Activity of Digesting a Protein Highly Resistant to Denaturation and Degradation (Particularly a Pathogenic Prion Protein)

The polynucleotide encoding the enzyme used in the present invention may be obtained, for example, by the following procedures. When a certain amino acid sequence is given, a nucleotide sequence encoding the amino acid sequence can be easily determined. Therefore, those skilled in the art can select various nucleotide sequences encoding the enzyme used in the present invention. The term "polynucleotide" as used herein includes DNA and RNA, preferably DNA.

The polynucleotide encoding the enzyme used in the present invention may be typically selected from the group consisting of:
(i) a polynucleotide comprising the nucleotide sequence of SEQ ID NO: 1 (preferably a polynucleotide consisting of the nucleotide sequence of SEQ ID NO: 1);
(ii) a polynucleotide comprising a nucleotide sequence in which one or plural (for example, one or several) nucleotides are deleted, substituted, or added in the nucleotide sequence of SEQ ID NO: 1, and encoding a protein exhibiting an activity of digesting a protein highly resistant to denaturation and degradation (particularly a pathogenic prion protein); and
(iii) a polynucleotide hybridizing under stringent conditions to a polynucleotide consisting of the nucleotide sequence of SEQ ID NO: 1, and encoding a protein highly resistant to denaturation and degradation (particularly a pathogenic prion protein).

In the polynucleotide described in the above item (ii), the number of nucleotides to be deleted, substituted, or added is, for example, 1 to 50, preferably 1 to 30, more preferably 1 to 18, most preferably 1 to 9.

The term "under stringent conditions" in the above item (iii) means the conditions in which a probe comprising the nucleotide sequence of SEQ ID NO: 1 is hybridized to a polynucleotide encoding the above-mentioned homologous protein, but the probe is not hybridized to that encoding keratinase derived from *Bacillus licheniformis* PWD-1 (U.S. Pat. No. 6,613,505) or a protease (such as thermoase) derived from *Bacillus thermoproteolyticus* Rokko.

More particularly, in accordance with a protocol attached to an ECL direct DNA/RNA labeling and detection system (Amersham), after a polynucleotide to be tested is prehybridized at 42° C. for an hour, a labeled probe having the full-length of the nucleotide sequence of SEQ ID NO: 1 is added, and hybridization is carried out at 42° C. for 15 hours. After the hybridization, a washing treatment with 0.4 or less×SSC (1×SSC; 15 mmol/L sodium citrate, 150 mmol/L sodium chloride) containing 0.4% SDS and 6 mol/L urea at 42° C. for 20 minutes is repeated twice, and a washing treatment with 5×SSC at room temperature for 10 minutes is carried out twice.

The polynucleotide encoding the enzyme used in the present invention includes a naturally-occurring polynucleotide. Further, the whole can be synthesized. Furthermore, the synthesis may be carried out using part of the naturally-occurring polynucleotide. Typically, the polynucleotide may be obtained by screening a genomic library derived from *Bacillus licheniformis* MSK-103 (FERM BP-08487) in accordance with an ordinary method commonly used in genetic engineering, for example, using an appropriate DNA probe designed on the basis of information of a partial amino acid sequence.

Expression Vector and Transformed Microorganism

The enzyme comprising the amino acid sequence of SEQ ID NO: 2, or the modified or homologous enzyme thereof, which may be used in the present invention, may be produced by an expression vector comprising a nucleotide sequence encoding the enzyme so that the nucleotide sequence may be replicated and the enzyme may be expressed. The expression vector can be constructed on the basis of a self-replicating vector (such as a plasmid), which exists as an extrachromosomal element and can replicate independently of the replication of chromosomes. Alternatively, the expression vector may be a vector which is integrated into the genome of the host microorganism and replicated together with chromosomes, when the host is transformed with the vector. The construction of the vector can be carried out by ordinary procedures or methods commonly used in genetic engineering.

To express a protein having a desired activity by transforming a host microorganism with the expression vector, it is preferable that the expression vector contains, for example, a polynucleotide capable of controlling the expression, or a genetic marker to select transformants, in addition to the polynucleotide encoding the enzyme used in the present invention. The polynucleotide capable of controlling the expression includes, for example, a promoter, a terminator, or a polynucleotide encoding a signal peptide. The promoter is not particularly limited, so long as it shows a transcriptional activity in a host microorganism. The promoter can be obtained as a polynucleotide which controls the expression of a gene encoding a protein the same as or different from that derived from the host microorganism. The genetic marker can be appropriately selected in accordance with the method for selecting a transformant. As the genetic marker, for example, a drug resistance gene or a gene complementing an auxotrophic mutation can be used.

The enzyme used in the present invention may be prepared by a microorganism transformed with the above expression vector. A host-vector system which can be used in the present invention is not particularly limited. For example, a system utilizing *E. coli*, Actinomycetes, yeasts, or filamentous fungi, or a system for the expression of a fusion protein using such a microorganism can be used. Transformation of a microorganism with the expression vector can be carried out in accordance with an ordinary method.

The transformant is cultivated in an appropriate medium, and the resulting host cells or culture is used to obtain the isolated enzyme used in the present invention. The transformant can be cultivated under the conditions commonly used in the cultivation thereof. Further, after the cultivation, the enzyme of interest can be collected in accordance with an ordinary method in the art.

The optimum process for producing the enzyme used in the present invention may be carried out by using preferably a microorganism belonging to genus *Bacillus*, more preferably *Bacillus licheniformis*, most preferably *Bacillus licheniformis* MSK-103 (FERM BP-08487) or a mutant thereof.

Enzyme Composition, and Agent for Digesting a Protein Highly Resistant to Denaturation and Degradation and Agent for Detoxifying a Pathogenic Prion Protein The enzyme composition or enzyme agent used in the present invention comprises at least an enzyme (hereinafter referred to as "enzyme used in the present invention") selected from the group consisting of the enzyme having the above-mentioned physical and chemical properties (including the enzyme obtained by a microorganism); the enzyme comprising the amino acid sequence of SEQ ID NO: 2, and the modified or homologous enzyme thereof; and the enzyme by cultivating the above-mentioned host cell.

The enzyme composition used in the present invention is not particularly limited, so long as it contains as an active ingredient the enzyme used in the present invention. The enzyme composition may be produced by mixing the active ingredient with a carrier or diluent commonly used in preparing an enzyme composition, such as fillers (for example, lactose, sodium chloride, or sorbitol), surfactants, or antiseptics, in a desired form such as powder or liquid.

The content of the enzyme in the enzyme composition is not particularly limited, so long as an activity thereof is sufficient for the purpose. The content may be 0.01 to 99% by weight, preferably 0.1 to 80% by weight.

With respect to an activity of digesting a protein highly resistant to denaturation and degradation, it is preferable that the enzyme composition exhibits 2 U/g or more (more preferably 2 to 500 U/g, still further preferably 10 to 500 U/g, most preferably 20 to 500 U/g) as an activity of digesting keratin azure, or 1 U/g or more (more preferably 1 to 5000 U/g, most preferably 5 to 3000 U/g) as an activity of digesting keratin powder. The amount of the enzyme is sufficient to digest a pathogenic prion protein contained in 1 mL of a 1% suspension containing a brain tissue derived from a mouse suffering from scrapie.

In addition to the enzyme used in the present invention, the enzyme composition used in the present invention may further contain at least one of enzymes other than the enzyme used in the present invention, such as a protease (for example, keratinase), lipase, cellulase, or xylanase. The use of the enzymes other than the enzyme used in the present invention is expected to develop the efficiency in digesting a pathogenic prion protein, in comparison with the enzyme composition containing the enzyme used in the present invention alone.

The enzyme used in the present invention exhibits an activity of digesting a protein highly resistant to denaturation and degradation (particularly a pathogenic prion protein). Therefore, the enzyme used in the present invention, or the enzyme composition used in the present invention containing the enzyme is useful as an active ingredient for an agent for digesting a protein highly resistant to denaturation and degradation (particularly a pathogenic prion protein), or as an active ingredient for an agent for detoxifying a pathogenic prion protein in a subject which may be contaminated with the pathogenic prion protein.

The agent of the present invention may contain as an active ingredient the enzyme used in the present invention alone, or together with an appropriate carrier and/or diluent. As the carrier or diluent, a conventional carrier or diluent which does not suppress or inhibit an activity of the enzyme used in the present invention, such as fillers (for example, lactose, sodium chloride, sodium sulfate, or sorbitol), surfactants, or antiseptics, can be used.

While the form of the agent of the present invention is not particularly limited, a foaming agent, which may be rapidly dissolved in water while foaming, is preferable. The formulation and preparation of the foaming agent are not particularly limited, but a conventional method may be used. The foaming agent may be prepared, for example, by mixing sodium bicarbonate, sodium percarbonate, or the like with an acid, such as citric acid, malic acid, or succinic acid, or by further adding thereto a mobilization agent such as silicic anhydride or other binders.

Method for Digesting a Protein Highly Resistant to Denaturation and Degradation (Particularly a Pathogenic Prion Protein)

The enzyme or enzyme composition used in the present invention may be used alone, or in the form of the above-mentioned agent of the present invention, to digest a protein highly resistant to denaturation and degradation (particularly a pathogenic prion protein), or to detoxify a pathogenic prion protein in a subject which may be contaminated with the pathogenic prion protein.

Therefore, the present invention includes a method for digesting a protein highly resistant to denaturation and degradation (particularly a pathogenic prion protein), using the enzyme or enzyme composition used in the present invention, and a method for detoxifying a pathogenic prion protein in a subject which may be contaminated with the pathogenic prion protein, using the enzyme or enzyme composition used in the present invention.

The method of the present invention for digesting a protein highly resistant to denaturation and degradation comprises at least the step of bringing the enzyme or enzyme composition used in the present invention into contact with a protein highly resistant to denaturation and degradation (particularly a pathogenic prion protein) or a subject to be digested which may contain the same. The method of the present invention for detoxifying a pathogenic prion protein comprises at least the step of bringing the enzyme or enzyme composition used in the present invention into contact with a subject to be detoxified which may be contaminated with a pathogenic prion protein.

As the subject to be digested or the subject to be detoxified (hereinafter collectively and simply referred to as "subject to be treated"), there may be mentioned, for example, feed which may contain a pathogenic prion protein (for example, meat and bone meal, or compost), instruments or equipment on which surfaces may be contaminated with a pathogenic prion protein (for example, instruments or equipment for slaughter, examination, or operations), or facilities in which a pathogenic prion protein may be present (for example, a slaughterhouse, a cowshed where BSE was present, or a laboratory for infection).

The subject to be treated may be used without preheating or with preheating (for example, at approximately 100° C. or more, preferably at 95° C. or more, more preferably at 90° C. or more, most preferably at 80° C. or more) before contact with the enzyme used in the present invention. According to the method of the present invention, a sufficient digestion or detoxification can be carried out without the preheating, and thus it is preferable that the subject to be treated is used without preheating (for example, at approximately 100° C. or more, at 95° C. or more, at 90° C. or more, or at 80° C. or more) before contact with the enzyme used in the present invention. When the preheating is not carried out, an additional apparatus for heating is not necessary, and procedures can be simplified.

The procedure of bringing the enzyme or enzyme composition used in the present invention into contact with the subject to be treated is not particularly limited and may be appropriately selected in accordance with the subject to be treated, so long as a protein highly resistant to denaturation and degradation (particularly a pathogenic prion protein), which may be contained in the subject to be treated, may be digested by the activity of the enzyme used in the present invention, i.e., an activity of digesting a protein highly resistant to denaturation and degradation (particularly a pathogenic prion protein).

For example, when the subject to be treated is feed which may contain a pathogenic prion protein, the contact may be carried out, for example, by uniformly mixing the enzyme or enzyme composition used in the present invention with the feed, or by spraying the feed with an aqueous solution containing the enzyme used in the present invention.

When the subject to be treated is an instrument on which a surface may be contaminated with a pathogenic prion protein, there may be mentioned, for example, a method of immersing the instrument in an aqueous solution containing the enzyme used in the present invention, a method of spraying the instrument with an aqueous solution containing the enzyme used in the present invention, or a method of washing the surface of the instrument with a washing tool (for example, a cloth, sponge, or brush) having an aqueous solution containing the enzyme used in the present invention.

When the subject to be treated is a facility in which a pathogenic prion protein may be present, the contact may be carried out, for example, by spraying an aqueous solution containing the enzyme used in the present invention.

It is preferable that the contact of the subject to be treated with the enzyme or enzyme composition used in the present invention is carried out under the conditions in which the enzyme used in the present invention may exhibit a sufficient activity of digesting a protein highly resistant to denaturation and degradation (particularly a pathogenic prion protein). For example, pH 7 to 12 is preferable. The contact may be carried out preferably at 20 to 80° C., more preferably 40 to 80° C.

The content of the enzyme used may be appropriately selected in accordance with the content of a protein highly resistant to denaturation and degradation (particularly a pathogenic prion protein) in the subject to be treated. For example, to digest a pathogenic prion protein contained in 1 mL of a 1% suspension containing a brain tissue derived from a mouse suffering from scrapie, it is preferable to use the enzyme composition containing 0.5 to 10 µg of the enzyme used in the present invention; the enzyme composition containing 2 U/g or more (more preferably 2 to 500 U/g, still further preferably 10 to 500 U/g, most preferably 20 to 500 U/g), as an activity of digesting keratin azure, of the enzyme used in the present invention; or the enzyme composition containing 1 U/g or more (more preferably 1 to 5000 U/g, most preferably 5 to 3000 U/g), as an activity of digesting keratin powder, of the enzyme used in the present invention. When the content of the enzyme is less than 0.5 µg, or the activity is less than 2 U/g or more (as an activity of digesting keratin azure) or less than 1 U/g (as an activity of digesting keratin powder), a complete digestion of the above content of the pathogenic prion protein becomes difficult. When the content of the enzyme is more than 10 μg, or the activity is more than 500 U/g or more (as an activity of digesting keratin azure) or more than 5000 U/g (as an activity of digesting keratin powder) to completely digest the above content of the pathogenic prion protein, it is not practically preferable from the viewpoint of production costs.

EXAMPLES

The present invention now will be further illustrated by, but is by no means limited to, the following Examples.

Example 1

Preparation of Purified Enzyme

In this example, cultivation and purification were carried out to obtain a purified enzyme used in the present invention as follows.

Culture medium A [1% polypeptone (Wako Pure Chemical Industries), 0.2% yeast extract (Difco), and 0.1% magnesium sulfate heptahydrate (Wako Pure Chemical Industries)(pH 7.0)] was autoclaved by a conventional method, and the medium A (200 mL) was inoculated with *Bacillus licheniformis* MSK-103 (FERM BP-08487). A cultivation was carried out at 37° C. under aeration and agitation for 72 hours. The resulting broth was centrifuged at 3000 G for 20 minutes to obtain a supernatant containing an enzyme used in the present invention.

The supernatant was concentrated 20-fold with an ultrafilter (5,000-molecular-weight cutoff) to obtain a concentrated supernatant containing the enzyme used in the present invention. The concentrated supernatant was filtered with a microfilter membrane (pore size=0.45 μm) to remove microorganisms. To the resulting sterile filtrate, ammonium sulfate was added to a final concentration of 1 mol/L, and a buffer agent (Tris-HCl) was further added to pH 8.5 and a final concentration of 50 mmol/L. For a further purification by a hydrophobic chromatography, the prepared solution was adsorbed to a phenyl Sepharose column, and eluted by a linear gradient with ammonium sulfate (1 mol/L to 0 mol/L) in a Tris-HCl buffer, to obtain a fraction containing the enzyme used in the present invention. The fraction was concentrated 20-fold with an ultrafilter (5,000-molecular-weight cutoff), and a gel filtration chromatography was carried out using Superdex 75 (Pharmacia) gel. The concentrated solution was developed through the gel with a phosphate buffer (0.025 mol/L, pH 7.0) containing 0.1 mol/L sodium chloride as an eluent, to obtain the enzyme used in the present invention. As a result, 20 μg of purified enzyme used in the present invention was obtained.

Example 2

Confirmation of Physical and Chemical Properties of the Enzyme (1) Activity and Substrate Specificity Activities of the purified enzyme obtained in Example 1 to various substrates (casein, collagen, elastin, and keratin) were examined. The results are shown in Table 2.

As shown in Table 2, the enzyme exhibited a high activity of digesting each substrate, particularly keratin. In this connection, the "1 unit (U)" of digestion activities compared in Table 2 is defined as an amount of the enzyme which can develop ninhydrin corresponding to 1 μmol of glycine per minute, under the following conditions:

Concentration of the substrate: 0.5%
pH: 9.0
Temperature: 60° C.

TABLE 2

| Substrate | Digestion activity (U) |
|---|---|
| casein | 326677 |
| collagen | 36958 |
| elastin | 10501 |
| keratin | 7187 |

(2) Molecular Weight

An SDS-polyacrylamide gel electrophoresis using a 12% homogeneous gel (Tefco) was carried out to determine a molecular weight of the purified enzyme prepared in Example 1. As a result, the molecular weight of the enzyme capable of digesting a pathogenic prion protein was approximately 31,000.

Another SDS-polyacrylamide gel electrophoresis using a 15% homogeneous gel (ATTO) was carried out to determine a molecular weight of the purified enzyme prepared in Example 1. As a result, the molecular weight of the enzyme capable of digesting a pathogenic prion protein was approximately 26,000. In this connection, Protein Molecular Weight Standard (Bio-Rad) was used as a standard marker in this example.

(3) Isoelectric Point

A polyacrylamide gel isoelectric focusing electrophoresis using an LKB electrophoresis system was carried out to determine an isoelectric point (pI) of the purified enzyme prepared in Example 1. As a result, the isoelectric point of the enzyme capable of digesting a pathogenic prion protein was 9.3. In this connection, each isoelectric point of standard samples used in this example is shown in Table 3.

TABLE 3

| Standard sample | Isoelectric point |
|---|---|
| trypsinogen | 9.30 |
| lentil lectin basic band | 8.65 |
| lentil lectin neutral band | 8.45 |
| lentil lectin acidic band | 8.15 |
| horse myoglobin basic band | 7.35 |
| horse myoglobin acidic band | 6.85 |
| human carbonic anhydrase B | 6.55 |
| horse carbonic anhydrase B | 5.80 |
| β-lactoglobulin A | 5.20 |
| soybean trypsin inhibitor | 4.55 |
| amyloglucosidase | 3.50 |

(4) Optimum pH and Stable pH

The optimum pH at 37° C. of purified enzyme prepared in Example 1, determined by an activity of digesting keratinazure (Sigma) as an index, was pH 9.0 to 10.0, as shown in FIG. 1. The stable pH at 37° C. of the enzyme was pH 7.0 to 12.0, preferably pH 8.0 to 10.5, as shown in FIG. 1.

(5) Optimum Temperature

Figure 2:
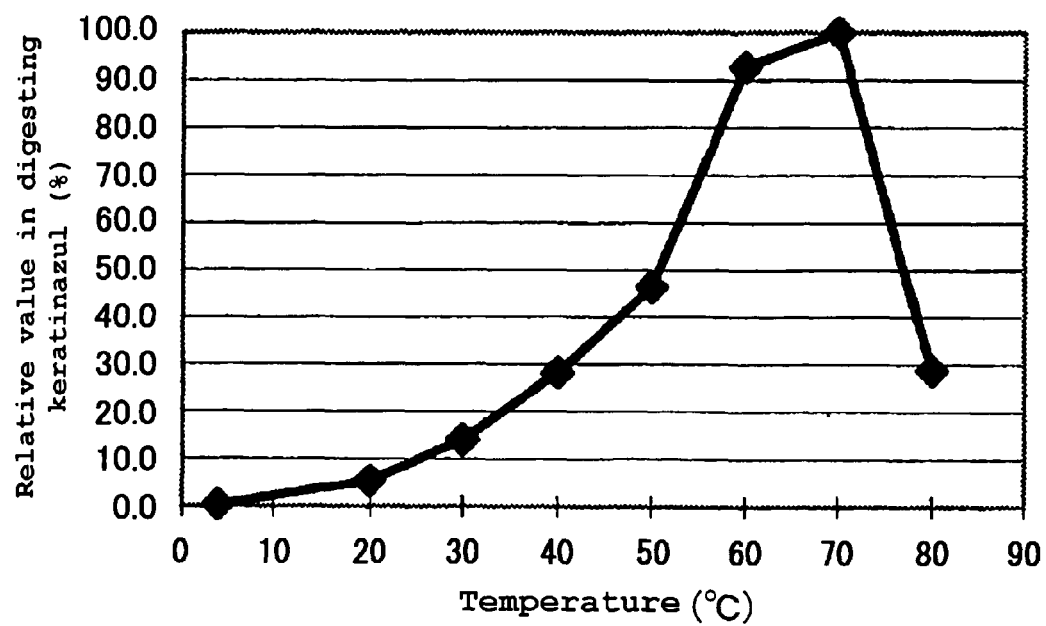
FIG. 2 is a graph showing the optimum temperature of a purified enzyme used in the present invention at pH 9.0.

The optimum temperature at pH 9.0 (i.e., optimum pH), determined by an activity of digesting keratin azure as an index, was 60 to 70° C., as shown in FIG. 2.

Example 3

Cloning of Enzyme Gene and Determination of Amino Acid Sequence Thereof

In this example, a gene encoding the purified enzyme prepared in Example 1 was cloned, and the nucleotide sequence of the gene was determined to confirm the amino acid sequence of the enzyme.

To purify the enzyme, the culture medium A (see Example 1) was inoculated with *Bacillus licheniformis* MSK-103 (FERM BP-08487). A cultivation was carried out at 37° C. for 3 days, and the resulting broth was centrifuged to obtain a supernatant. The supernatant was concentrated approximately 20-fold with Pellicon XL (cut 5000; Millipore), and was adjusted to a solution containing 1 mol/L magnesium sulfate and 0.05 mol/L Tris-HCl (pH8.5). The prepared solution was applied to a phenyl Sepharose column (Phenyl Sepharose FF; low sub, 26×300 mm; Amersham Bioscience), and eluted by a linear concentration gradient with ammonium sulfate (1 mol/L to 0 mol/L) in a 0.05 mol/L Tris-HCl buffer (pH8.5), to obtain a fraction eluted with 0 mol/L of ammonium sulfate. The fraction was concentrated with Pellicon XL (cut 5000) followed by Ultrafree 15 (Ucut5000; Millipore). The concentrated solution was applied to Superdex (Superdex75pg; 16×600 mm; Amersham Bioscience), and eluted with a phosphate buffer (0.05 mol/L, pH 7.0) containing 0.1 mol/L sodium chloride to obtain a fraction having a molecular weight of approximately 31 kDa. It was confirmed by SDS-PAGE that the fraction contained, as a single substance, a protein having a molecular weight of approximately 31 kDa.

The purified protein was subjected to SDS-PAGE, and transferred to a polyvinylidene difluoride (PVDF) membrane (Immobilon PSQ; Millipore), to blot the protein on the PVDF membrane. The PVDF membrane was washed with water and air-dried, and then was used to analyze the amino acid sequence of the protein by a protein sequencer (Model 492; Applied Biosystems). As a result, the following amino acid sequence was obtained:

N-terminal amino acid: AQTVPYGIPLI (the sequence consisting of the 1st to 11th amino acids in the amino acid sequence of SEQ ID NO: 2)

It was found that the obtained amino acid sequence is the same sequence as those of keratinase derived from *Bacillus licheniformis* PWD-1 [Lin, X. et. al., Appl. Environ. Microbiol (1995) 61, 1469-1474] and subtilisin carlsberg derived from *Bacillus licheniformis* [Jacobs, M. et. al., Nucleic Acid Res. (1985) 13, 8913-8926]. Next, a partial fragment was amplified by PCR, and was used as a probe to clone a gene of interest as follows.

Genomic DNA derived from *Bacillus licheniformis* MSK-103 (FERM BP-08487) was prepared in accordance with a method of Wilson et al. [Wilson, C. R., J. Bacteriol. (1985) 163, 445-453]. A PCR using the genome DNA as a template and a combination of the following primers was carried out to amplify a partial fragment of a gene encoding the enzyme capable of digesting an abnormal prion. The PCR was carried out by using Takara Taq (Takara Bio) as an enzyme for PCR, and by performing a heat denaturation at 94° C. for a minute, followed by repeating a cycle consisting of reactions at 94° C. for 30 seconds, at 48° C. for 30 seconds and at 68° C. for 2 minutes 30 times, to amplify the DNA of interest. Primer PDE-2 for partial fragment amplification:

5'-agagcggcggaaaagtggac-3' (SEQ ID NO: 3) Primer PDE-5 for partial fragment amplification:

5'-cctgcgccaggagccatgac-3' (SEQ ID NO: 4)

As a result, a fragment of approximately 700 bp was amplified. The amplified DNA fragment was used as a probe to clone the full-length of the gene of interest from a genomic library derived from *Bacillus licheniformis* MSK-103 (FERM BP-08487) as follows.

Genomic DNA derived from *Bacillus licheniformis* MSK-103 (FERM BP-08487) was partially digested with restriction enzyme Sau IIIA1, and the fragments were ligated into an EMBLIII vector (Stratagene). A commercially available packaging kit (MaxPlax Lambda packaging extract; Epicentre technologies) was used to form phage particles containing the constructs. The obtained phage library was screened by using a commercially available screening kit (DIG high prime DNA labeling and detection starter kit; Roche) to obtain 100 positive clones from approximately 10000 plaques. DNAs were purified from 10 positive clones, an SphI fragment of approximately 4.1 kb, which was contained in 4 positive clones thereamong, was subcloned into pUC119 to construct pUC-PDE4. The size of the SphI fragment accorded with a result of a Southern analysis of *Bacillus licheniformis* MSK-103 (FERM BP-08487) using the PCR product as a probe. The plasmid pUC-PDE4 was used to determine the DNA sequence thereof by a shotgun sequence method using a DNA sequencer (model 3730XL; Applied Biosystems). As a result, the plasmid contained the full-length of the gene encoding the enzyme capable of digesting an abnormal prion, and the nucleotide sequence of the coding region was that of SEQ ID NO: 1.

As a result, it was confirmed that the amino acid sequence of the purified enzyme obtained in Example 1 is completely identical to that of subtilisin DY (WO98/30682). Further, the second highest homology was 81% in a kerA gene derived from *Bacillus licheniformis* (by a BLAST search).

Example 4

Preparation of Enzyme Composition

To obtain an enzyme composition used in the present invention, the culture medium A (200 mL) described in Example 1 was inoculated with *Bacillus licheniformis* MSK-103 (FERM BP-08487). A cultivation was carried out at 37° C. under aeration and agitation for 48 hours. The obtained broth was centrifuged at 3000G for 30 minutes to obtain a supernatant containing the enzyme used in the present invention. The supernatant was concentrated 30-fold with an ultrafilter (5,000-molecular-weight cutoff) to obtain a concentrated supernatant. The concentrated supernatant was filtered with a microfilter (pore size=0.45 µm) to remove microorganisms. As a result, a solution of enzyme composition A containing the enzyme used in the present invention was obtained. The enzyme composition A exhibited an activity of digesting keratinazure, and the activity was 285 U/g. The solution of the enzyme composition A was lyophilized to obtain powder of enzyme composition A'.

Culture medium B [0.01% yeast extract (Difco), 1% feather meal (ITOCHU FEED MILLS CO., LTD), 0.01% magnesium chloride (Wako Pure Chemical Industries), 0.04% dipotassium hydrogen phosphate (Wako Pure Chemical Industries), 0.03% potassium dihydrogen phosphate (Wako Pure Chemical Industries), 0.05% sodium chloride (Wako Pure Chemical Industries), and 0.05% ammonium chloride (Wako Pure Chemical Industries)(pH 7.0)] was autoclaved, and the medium B (40 mL) was inoculated with *Bacillus licheniformis* PWD-1 (ATCC-53757). A cultivation was carried out at 37° C. under aeration and agitation for 48 hours. The resulting broth was centrifuged at 3000 G for 30 minutes to obtain a supernatant. The supernatant was concentrated 18-fold with an ultrafilter (5,000-molecular-weight cutoff) to obtain a concentrated supernatant. The concentrated supernatant was filtered with a microfilter (pore size=0.45 μm) to remove microorganisms. As a result, a solution of enzyme composition B for comparison was obtained.

Example 5

Digestion of Mouse Pathogenic Prion Protein with Purified Enzyme

In this example, the purified enzyme used in the present invention prepared in accordance with the method described in Example 1, and a commercially available protease (subtilisin carlsberg; Sigma) were used to evaluate an activity of digesting a pathogenic prion protein. In this connection, an activity of an enzyme preparation (proteinase K; Wako Pure Chemical Industries) was used as a standard.

As a substrate used in this example, the brain derived from a mouse infected with the pathogenic prion protein [CLINICAL AND DIAGNOSTIC LABORATORY IMMUNOLOGY, (USA), American Society for Microbiology (Asm), March in 1995, p. 172-176] was used to prepare a 5% homogenate [2% N-sodium lauroyl sarcosinate, and 10 mmol/L Tris-HCl buffer (pH 7.5)], and the 5% homogenate was diluted to a final concentration of 1% with 50 mmol/L Tris-HCl buffer (pH 8.3).

An enzyme reaction was carried out by mixing the 1% brain homogenate with an equal volume of the purified enzyme solution, the commercially available protease solution, or the enzyme preparation solution, and incubating each mixture at 37° C. for 1 hour. The concentrations of the purified enzyme, the commercially available protease, and the enzyme preparation were 1 μg/mL and 0.2 μg/mL, as a final concentration in each reaction mixture during the enzyme reaction.

An aliquot of each reaction mixture after the enzyme reaction was used to carry out a sodium dodecyl sulfate-polyacrylamide gel electrophoresis (SDS-PAGE) using a electrophoresis system (ATTO) and an SDS-polyacrylamide gel (10% gel; ATTO). Proteins in the polyacrylamide gel after SDS-PAGE were transferred to a polyvinylidene difluoride (PVDF) membrane (Millipore) by a blotting system (ATTO) in accordance with a protocol attached thereto. The pathogenic prion protein bound to the PVDF membrane was labeled by an antibody-antigen method using an anti-prion-protein rabbit antibody as the first antibody, and a horseradish-peroxidase-labeled anti-rabbit-IgG goat antibody (Zymed) as the second antibody. The pathogenic prion protein was detected by a commercially available labeling and detecting kit (ECL+Plus Western Blotting Detection System; Amersham Bioscience) in accordance with a protocol attached thereto.

In this connection, the anti-prion-protein rabbit antibody used as the first antibody was prepared as follows. A peptide (PrP94-112) consisting of 20 amino acids in which cystein (Cys) was added to an N-terminal sequence of a core fragment P27-30 of sheep scrapie prion protein was synthesized, and a rabbit was immunized with the peptide conjugated to Keyhole limpet hemocyanin (KLH) as an immunogen. The obtained rabbit antiserum was subjected to a protein A column to purify the antibody of interest. The antibody reacts to not only sheep prion protein but also hamster, mouse, and bovine prion proteins.

Figure 3:
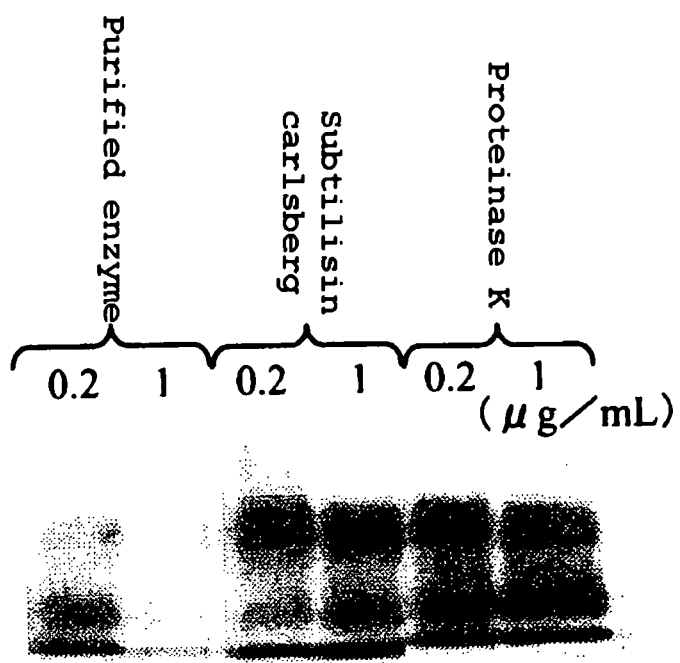
FIG. 3 shows the results in which the mouse pathogenic prion protein was digested with a purified enzyme used in the present invention.

The results are shown in FIG. 3. When using proteinase K as a standard, or subtilisin carlsberg as a commercially available protease, bands resistant to proteases, which indicated the presence of the pathogenic prion protein, were detected even at the concentration of 1 μg/mL. The molecular weight of the band not digested at all was 32 kDa, and those of partially-digested bands (three bands) were 30 kDa, 25-26 kDa, and 20-21 kDa. In contrast, when using the purified enzyme used in the present invention, a band was detected at 0.2 μg/mL, but almost all the pathogenic prion proteins contained in the 1% brain homogenate were digested at 1 μg/mL.

Example 6

Digestion of Mouse Pathogenic Prion Protein with Enzyme Composition

In this example, the solution of enzyme composition A used in the present invention prepared in accordance with the method described in Example 4 was used to evaluate an activity of digesting mouse pathogenic prion protein. In this connection, an activity of an enzyme preparation (proteinase K; Wako Pure Chemical Industries) was used as a standard. As a substrate, the same substrate used in Example 5 (i.e., 1% brain homogenate derived from a mouse infected with the pathogenic prion protein) was used.

An enzyme reaction was carried out by mixing the 1% brain homogenate with an equal volume of the enzyme composition solution or the enzyme preparation solution, and incubating each mixture at 37° C. for 1 hour. The concentrations of the enzyme preparation were 50 μg/mL, 25 μg/mL, 12.5 μg/mL, and 6.25 μg/mL, as a final concentration. As to the enzyme composition A, the original solution was diluted to 1, ½, ¼, ⅛, and 1/16. The diluted solutions exhibited 285 U/g, 143 U/g, 71 U/g, 36 U/g, and 18 U/g as an activity of digesting keratin azure, respectively.

An aliquot of each reaction mixture after the enzyme reaction was used to detect the pathogenic prion protein in accordance with the method described in Example 5.

Figure 4:
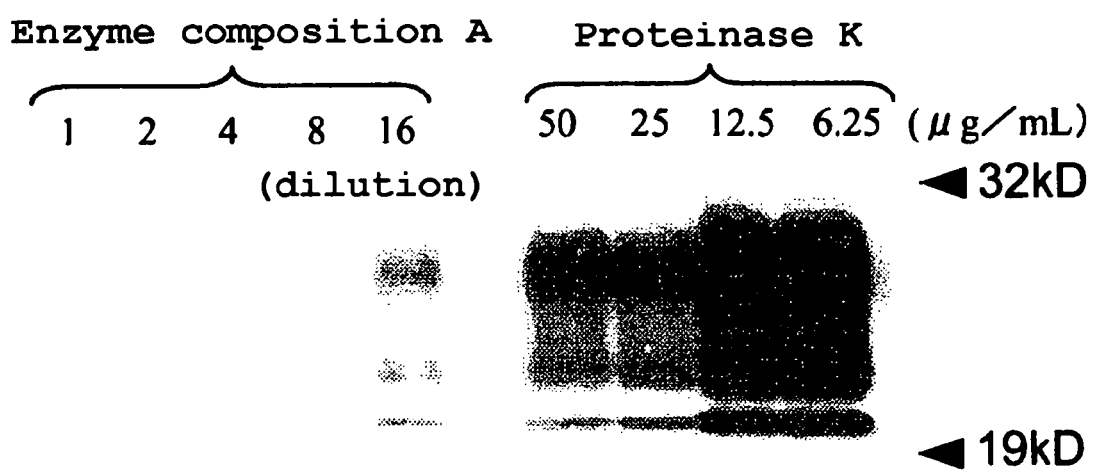
FIG. 4 shows the results in which the mouse pathogenic prion protein was digested with enzyme composition A used in the present invention.

The results are shown in FIG. 4. When using proteinase K as a standard, bands resistant to proteases, which indicated the presence of the pathogenic prion protein, were detected even at a high concentration of 50 μg/mL. In contrast, when using the enzyme composition used in the present invention, a band was slightly detected at 18 U/g as an activity of digesting keratin azure (diluted to 1/16; a 1.875-fold concentrated solution of the broth), but the pathogenic prion protein was completely digested at 36 U/g (diluted to ⅛; a 3.75-fold concentrated solution of the broth) or more.

Example 7

Digestion of Sheep Pathogenic Prion Protein with Enzyme Composition

In this example, the solution of enzyme composition A used in the present invention and the solution of enzyme composition B (containing keratinase derived from *Bacillus licheniformis* PWD-1) for comparison, each being prepared in accordance with the method described in Example 4, were used to evaluate an activity of digesting sheep pathogenic prion protein. In this connection, an activity of an enzyme preparation (proteinase K; Wako Pure Chemical Industries) was used as a standard.

As a substrate used in this example, the brain derived from a sheep infected with the pathogenic prion protein was used to prepare a 5% homogenate [2% N-sodium lauroyl sarcosinate, and 10 mmol/L Tris-HCl buffer (pH 7.5)], and the 5% homogenate was diluted to a final concentration of 1% with 50 mmol/L Tris-HCl buffer (pH 8.3).

An enzyme reaction was carried out by mixing the 1% brain homogenate with an equal volume of the enzyme composition solution or the enzyme preparation solution, and incubating each mixture at 37° C. for 1 hour. The concentrations of the enzyme preparation were 50 μg/mL, 10 μg/mL, 2 μg/mL, and 0.4 μg/mL, as a final concentration. As to the enzyme composition A used in the present invention, the original solution was diluted to 1, ½, ¼, and ⅛. The diluted solutions exhibited 285 U/g, 143 U/g, 71 U/g, and 36 U/g as an activity of digesting keratin azure, respectively. As to the enzyme composition B for comparison, the original solution was diluted to 1, ½, ¼, and ⅛. The diluted solutions exhibited 37 U/g, 19 U/g, 9 U/g, and 5 U/g.

An aliquot of each reaction mixture after the enzyme reaction was used to detect the pathogenic prion protein in accordance with the method described in Example 5.

Figure 5:
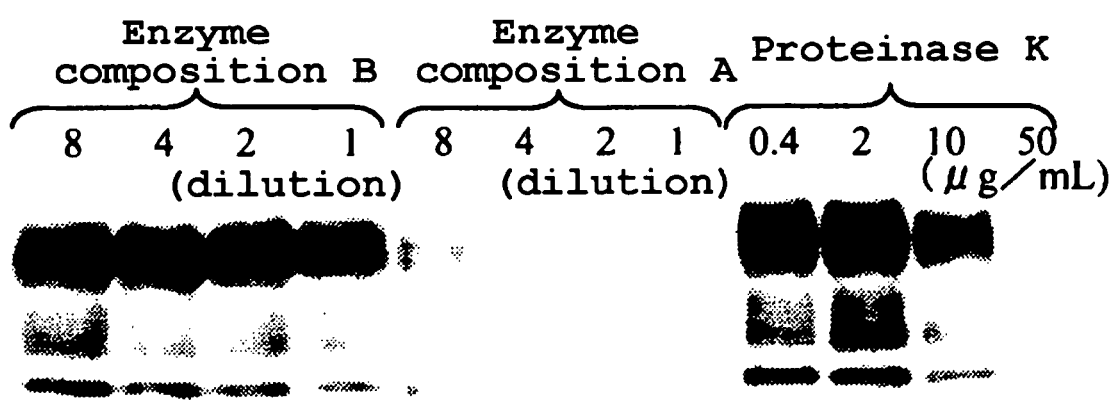
FIG. 5 shows the results in which the sheep pathogenic prion protein was digested with enzyme composition A used in the present invention.

The results are shown in FIG. 5. When using proteinase K as a standard, bands resistant to proteases, which indicated the presence of the pathogenic prion protein, were detected at the concentrations of 10 μg/mL or less. When using the enzyme composition B for comparison, the pathogenic prion protein was not digested at any concentration. In contrast, when using the enzyme composition A used in the present invention, the pathogenic prion protein was almost completely digested at any concentration. In addition, it was found that the enzyme of the present invention can digest a pathogenic prion protein derived from a different species and having a different amino acid sequence with a minor variation.

Example 8

Digestion of Mouse Pathogenic Prion Protein with Enzyme Composition

*Bacillus licheniformis* PWD-1 was cultivated in accordance with the method described in Example 4 for preparing the enzyme composition A used in the present invention (i.e., using the medium A), and an enzyme composition C for comparison was prepared in accordance with the method described in Example 4 for preparing the enzyme composition A.

Further, *Bacillus licheniformis* DSM-8782 was cultivated in accordance with the method described in Example 4 for preparing the enzyme composition A used in the present invention (i.e., using the medium A), and an enzyme composition D for comparison was prepared in accordance with the method described in Example 4 for preparing the enzyme composition A.

Furthermore, *Bacillus licheniformis* DSM-8782 was cultivated in accordance with the method described in Example 4 for preparing the enzyme composition B for comparison (i.e., using the medium B), and an enzyme composition E for comparison was prepared in accordance with the method described in Example 4 for preparing the enzyme composition B.

In Table 4, the relationships of the enzyme compositions to the strains and the media are shown. The medium B is a medium for inducing keratinase [Japanese Unexamined Patent Publication (Kokai) No. 6-46871].

TABLE 4

| Enzyme composition | Strain | Medium |
| --- | --- | --- |
| A | FERM BP-08487 | A |
| B | PWD-1 | B |
| C | PWD-1 | A |
| D | DSM-8782 | A |
| E | DSM-8782 | B |

The resulting enzyme composition A used in the present invention and four enzyme compositions B to E for comparison were used to compare the activity of digesting mouse pathogenic prion protein, in accordance with the procedures described in Example 7, except that a final concentration of each enzyme composition was concentrated 18-fold with respect to each supernatant.

Figure 6:
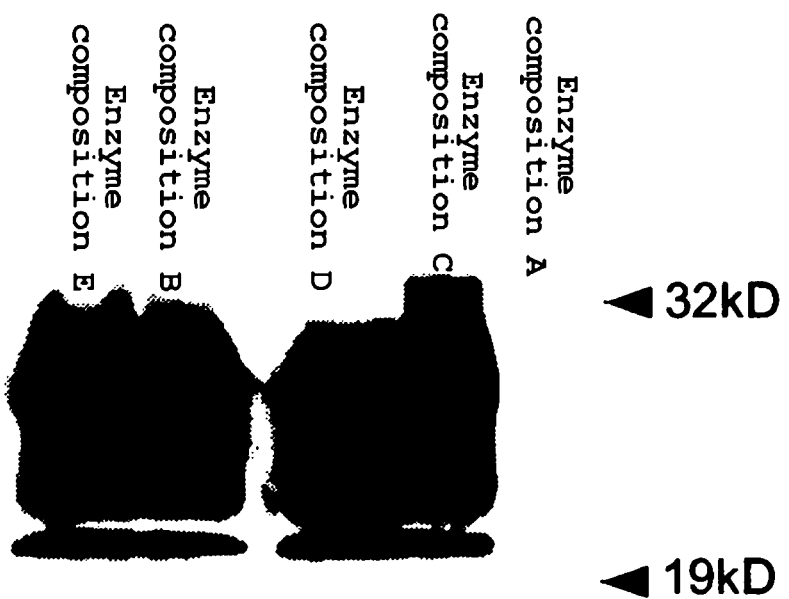
FIG. 6 shows the results in which the mouse pathogenic prion protein was digested with enzyme composition A used in the present invention.

The results are shown in FIG. 6. As shown in FIG. 6, the pathogenic prion protein was not digested by the enzyme compositions B to E for comparison, but was completely digested by the enzyme composition A used in the present invention.

Example 9

Comparative Test to Thermoase (1)

The enzyme composition A' used in the present invention prepared in accordance with the procedures described in Example 4, and thermoase (DAIWA KASEI K.K.), as an enzyme for comparison, derived from *Bacillus thermoproteolyticus* Rokko disclosed in WO02/053723 were used to evaluate the activity of digesting hamster pathogenic prion protein (strain Sc237).

As a substrate used in this example, the brain derived from a mouse infected with hamster-type pathogenic prion protein (strain Sc237) was used to prepare a 1% brain homogenate [50 mmol/L Tris-HCl buffer (pH 8.3)]. The Sc237-type pathogenic prion protein was accumulated in the brain of the mouse.

Each enzyme solution was prepared by dissolving the enzyme composition A' or thermoase in a 50 mmol/L Tris-HCl buffer (pH8.3). The concentrations of each solution were 4, 8, 16, and 32 U/mL (as a final concentration) as an activity of digesting keratin powder.

The enzyme reaction was carried out by mixing the 1% brain homogenate with an equal volume of each enzyme solution, and incubating the mixture at 37° C. for 20 hours.

An aliquot of each reaction mixture after the enzyme reaction was used to detect the pathogenic prion protein in accordance with the method described in Example 5.

Figure 7:
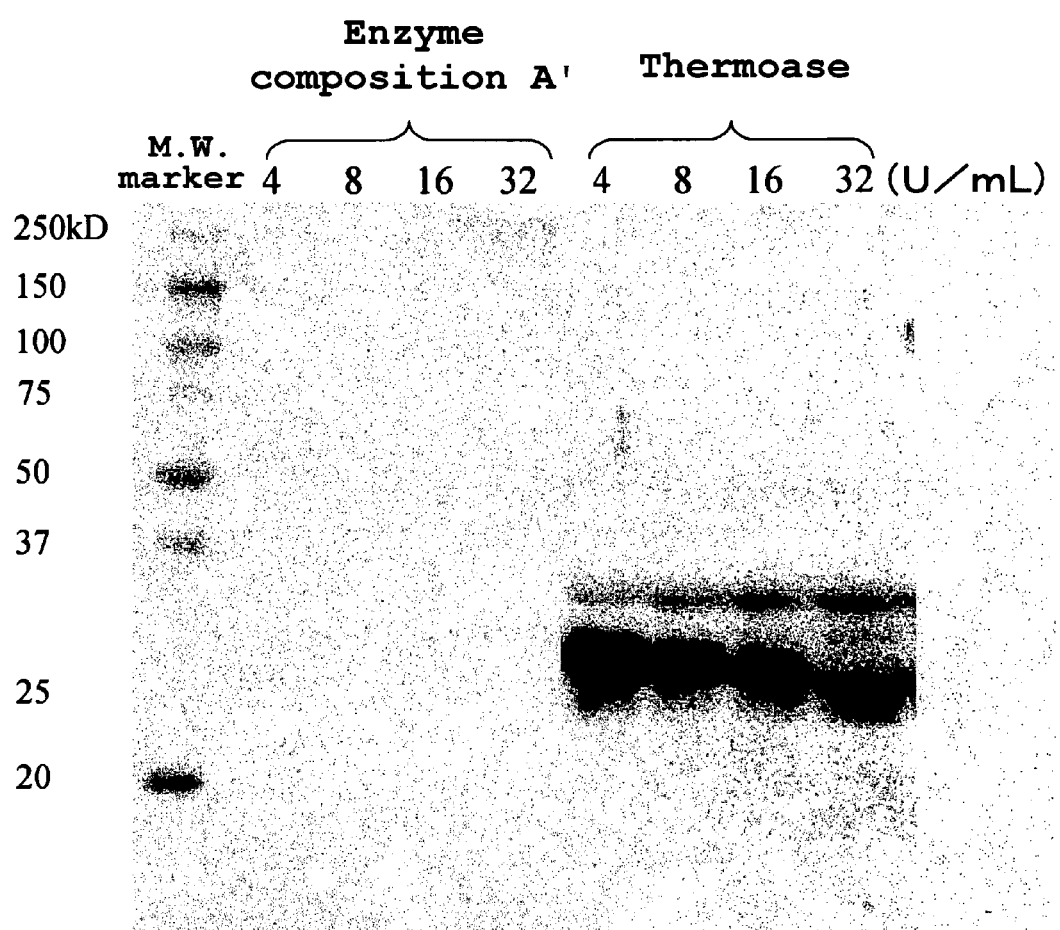
FIG. 7 shows the results in which the hamster pathogenic prion protein (strain Sc237) was digested with enzyme composition A' used in the present invention or thermoase for comparison.

The results are shown in FIG. 7. When using the enzyme solution containing thermoase, bands resistant to proteases, which indicated the presence of the pathogenic prion protein, were detected at any concentration. In contrast, when using the enzyme composition used in the present invention, the pathogenic prion protein was completely digested below the levels of detection by Western blotting, at any concentration.

Example 10

Comparative Test to Thermoase (2)

WO02/053723 discloses that an activity of thermoase in digesting a protein (a pathogenic prion protein derived from BSE) is increased in the presence of sodium dodecyl sulfate (SDS). In this example, an activity of digesting hamster pathogenic prion protein was evaluated under such conditions.

The enzyme composition A' used in the present invention prepared in accordance with the procedures described in Example 4, and the thermoase solution used in Example 9 were used to evaluate the activity of digesting hamster pathogenic prion protein (strain Sc237).

As a substrate used in this example, the brain derived from a mouse infected with hamster-type pathogenic prion protein (strain Sc237) was used to prepare a 1% brain homogenate [50 mmol/L Tris-HCl buffer (pH 8.3) containing 0.1, 1, or 4% SDS (final concentrations of SDS in the following reaction=0.05, 0.5, or 2%)]. The Sc237-type pathogenic prion protein was accumulated in the brain of the mouse.

The enzyme reaction was carried out by mixing the 1% brain homogenate with an equal volume of each enzyme solution, and incubating the mixture at 37° C. for 20 hours. The concentration of each solution was 4 U/mL (as a final concentration) as an activity of digesting keratin powder.

An aliquot of each reaction mixture after the enzyme reaction was used to detect the pathogenic prion protein in accordance with the method described in Example 5.

The results are shown in FIG. 8. In FIG. 8, lane 1 is thermoase (4 U/mL; 0.05% SDS), lane 2 is thermoase (4 U/mL; 0.5% SDS), lane 3 is thermoase (4 U/mL; 2% SDS), and lane 4 is the enzyme composition A' solution (4 U/mL; 2% SDS).

When using the enzyme solution containing thermoase, bands resistant to proteases, which indicated the presence of the pathogenic prion protein, were detected even at the final concentration of 2% SDS. In contrast, when using the enzyme composition used in the present invention, the pathogenic prion protein was completely digested below the levels of detection by Western blotting, at any concentration.

As described above, it is found that the enzyme used in the present invention exhibits an excellent activity of digesting a pathogenic prion protein even in the presence of SDS, in comparison with thermoase.

Example 11

Washing Model Test Using Microplate

To evaluate the effects on washing instruments contaminated with a pathogenic prion protein, a model test was carried out as follows.

The enzyme composition A' used in the present invention prepared in accordance with the procedures described in Example 4, and the thermoase solution used in Example 9 were used to evaluate the activity of digesting hamster pathogenic prion protein (strain Sc237) stuck on polystyrene.

As a substrate used in this example, the brain derived from a mouse infected with a hamster-type pathogenic prion protein (strain Sc237) was used to prepare a 1% brain homogenate [50 mmol/L Tris-HCl buffer (pH 8.3)]. The Sc237-type pathogenic prion protein was accumulated in the brain of the mouse. As a control, a normal brain not infected with the abnormal prion protein was used to prepare a 1% brain homogenate [50 mmol/L Tris-HCl buffer (pH 8.3)].

Each 1% brain homogenate (25 µL/well) of normal or Sc237-infected hamster was added to a polystyrene microplate (IMMUNO MODULE; Nunc), and the plate was completely dried at room temperature for one day.

To carry out a washing treatment of the resulting microplate using enzyme solutions, the enzyme composition A' and thermoase were diluted to 7.5 U/mL and 15 U/mL (as an activity of digesting keratin powder) with 50 mmol/L Tris-HCl buffer (pH8.3) to prepare a washing solution A (7.5 U/mL) and washing solution B (15 U/mL), respectively.

The enzyme reaction was carried out by adding 100 µL/well of each washing solution, and incubating the plate at 37° C. for 1 hour under shaking at 100 rpm. Each washing solution was removed, and each well was washed twice with approximately 300 µL of PBS.

A denature treatment was carried out by adding 100 µL/well of 6 mol/L guanidine hydrochloride (Wako Pure Chemical Industries) and allowing the plate to stand at room temperature for 1 hour. Each well was washed three times with approximately 300 µL of PBS to remove guanidine hydrochloride. Blocking was carried out by adding 300 µL/well of 5% skimmed milk (Amersham) and allowing the plate to stand at room temperature for 1 hour. Each well was washed twice with approximately 300 µL of 0.05% Tween 20-PBS.

The pathogenic prion protein bound to the microplate was labeled by an antibody-antigen method using an anti-prion-protein mouse antibody (3F4; Chemicon International) as the first antibody, and a horseradish-peroxidase-labeled anti-mouse-IgG goat antibody (Zymed) as the second antibody. The prion protein remaining in each well of the microplate was detected by a luminescent reaction using a commercially available labeling and detecting kit (Super Signal West Dura; Amersham Bioscience) in accordance with a protocol attached thereto. The amount of luminescence was recorded by a light capture (AE-6962; ATTO), and an image analysis was carried out by a software for image analysis (CS Analyzer; ATTO).

Figure 9:
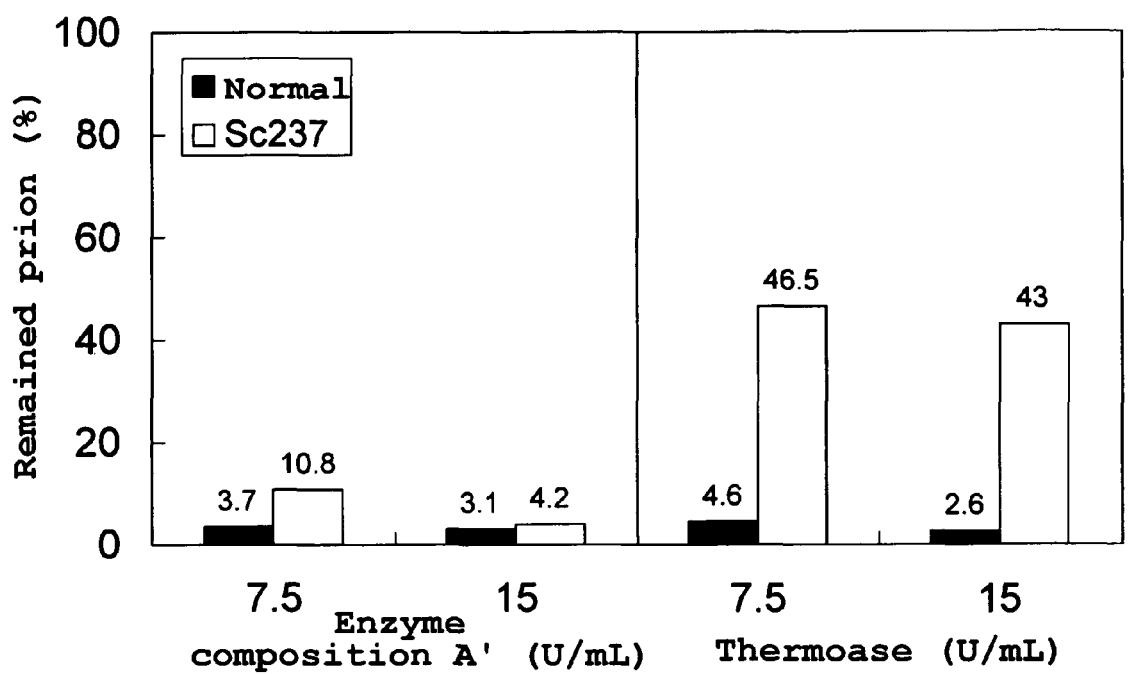
FIG. 9 shows the results in which the hamster pathogenic prion protein (strain Sc237) stuck on polystyrene was digested with enzyme composition A' used in the present invention or thermoase for comparison.

The results are shown in FIG. 9. When using the enzyme composition used in the present invention, a residual rate of the pathogenic prion protein was less than 10% at the concentration of 7.5 U/mL, and the rate was less than approximately 1% at the concentration of 15 U/mL. In contrast, when using thermoase, the rate was 40% or more at any concentration. As a result, it was found that the enzyme used in the present invention exhibits an excellent activity of washing away a pathogenic prion protein.

INDUSTRIAL APPLICABILITY

The enzyme used in the present invention exhibits an excellent activity of digesting a protein highly resistant to denaturation and degradation (particularly a pathogenic prion protein) in comparison with known proteases. Therefore, according to the enzyme used in the present invention or the enzyme composition used in the present invention containing the enzyme, a pathogenic prion protein can be efficiently digested. Further, the enzyme used in the present invention can be produced at a low cost.

According to the enzyme or the enzyme composition, contamination in a subject which may be contaminated with a pathogenic prion protein can be removed. The enzyme is useful as an active ingredient for an agent of the present invention for digesting or detoxifying a pathogenic prion protein.

FREE TEST IN SEQUENCE LISTING

Features of "Artificial Sequence" are described in the numeric identifier <223> in the Sequence Listing. More particularly, the nucleotide sequence of SEQ ID NO: 3 is primer PDE-2, and the nucleotide sequence of SEQ ID NO: 4 is primer PDE-5.

Although the present invention has been described with reference to specific embodiments, various changes and modifications obvious to those skilled in the art are possible without departing from the scope of the appended claims.

The invention claimed is:

1. A method for detoxifying a pathogenic prion protein, comprising the step of bringing a surface which may be contaminated with a pathogenic prion protein into contact with an enzyme exhibiting an activity of digesting a protein highly resistant to denaturation and degradation and having the following properties:
   (a) activity and substrate specificity: hydrolyzing a peptide bond of a protein highly resistant to denaturation and degradation;
   (b) molecular weight: 31,000 (determined by an SDS-polyacrylamide gel electrophoresis using a homogeneous gel having a gel concentration of 12%);
   (c) isoelectric point: pI 9.3 (determined by polyacrylamide gel isoelectric focusing electrophoresis);
   (d) optimum pH: pH 9.0 to 10.0; and
   (e) optimum temperature for activity: 60 to 70° C.,
   wherein the contacting step is carried out without preheating the subject, and said enzyme is produced by *Bacillus licheniformis* MSK-103 (FERM BP-08487).

2. The method according to claim 1, wherein the contacting step is carried out without preheating the subject at 90° C. or more.

3. The method according to claim 1, wherein the enzyme has the following property:
   (g) exhibiting an activity of 2 U/g or more as the activity of digesting a protein highly resistant to denaturation and degradation (determined as an activity of digesting keratin azure).

4. The method according to claim 1, wherein the enzyme is selected from the group consisting of
   (X) an enzyme comprising the amino acid sequence of SEQ ID NO: 2;
   (Y) a modified enzyme exhibiting an activity of digesting a protein highly resistant to denaturation and degradation, and comprising an amino acid sequence in which one or plural amino acids are deleted, substituted, or added in the amino acid sequence of SEQ ID NO: 2; and
   (Z) a homologous enzyme exhibiting an activity of digesting a protein highly resistant to denaturation and degradation, and comprising an amino acid sequence having an 85% or more homology with the amino acid sequence of SEQ ID NO: 2.

5. The method according to claim 1, wherein the protein highly resistant to denaturation and degradation is a pathogenic prion protein.

6. The method according to claim 3, wherein the contacting step is carried out without preheating the subject at 90° C. or more.

7. The method according to claim 4, wherein the contacting step is carried out without preheating the subject at 90° C. or more.

8. The method according to claim 5, wherein the contacting step is carried out without preheating the subject at 90° C. or more.

* * * * *

UNITED STATES PATENT AND TRADEMARK OFFICE
CERTIFICATE OF CORRECTION

PATENT NO. : 7,776,579 B2  Page 1 of 1
APPLICATION NO. : 10/532605
DATED : August 17, 2010
INVENTOR(S) : Takehiro Miwa et al.

It is certified that error appears in the above-identified patent and that said Letters Patent is hereby corrected as shown below:

In claim 1 at column 29, line 37:
Delete "subject" and insert --surface--

In claim 2 at column 29, line 40:
Delete "subject" and insert --surface--

In claim 6 at column 30, line 37:
Delete "subject" and insert --surface--

In claim 7 at column 30, line 40:
Delete "subject" and insert --surface--

In claim 8 at column 30, line 43:
Delete "subject" and insert --surface--

Signed and Sealed this
Twenty-eighth Day of December, 2010

David J. Kappos
*Director of the United States Patent and Trademark Office*

```
                              SEQUENCE LISTING

<160> NUMBER OF SEQ ID NOS: 4

<210> SEQ ID NO 1
<211> LENGTH: 825
<212> TYPE: DNA
<213> ORGANISM: Bacillus Licheniformis
<220> FEATURE:
<221> NAME/KEY: CDS
<222> LOCATION: (1)..(825)

<400> SEQUENCE: 1 gcc caa aca gtt cct tac ggc atc ccg ctc atc aag gct gac aaa gtg        48
Ala Gln Thr Val Pro Tyr Gly Ile Pro Leu Ile Lys Ala Asp Lys Val
1               5                   10                  15 cag gcc caa ggt tat aaa ggg gca aat gtc aaa gtc ggt atc att gat        96
Gln Ala Gln Gly Tyr Lys Gly Ala Asn Val Lys Val Gly Ile Ile Asp
            20                  25                  30 acg gga atc gct tcg tct cat aca gac ttg aag gta gtc ggc gga gca       144
Thr Gly Ile Ala Ser Ser His Thr Asp Leu Lys Val Val Gly Gly Ala
        35                  40                  45 agc ttt gta tct ggt gaa agt tat aat acg gac ggt aac gga cac ggc       192
Ser Phe Val Ser Gly Glu Ser Tyr Asn Thr Asp Gly Asn Gly His Gly
    50                  55                  60 aca cat gtt gcc gga aca gtg gcg gcg ctt gac aat aca aca ggc gtt       240
Thr His Val Ala Gly Thr Val Ala Ala Leu Asp Asn Thr Thr Gly Val
65                  70                  75                  80 tta ggc gtt gca ccg aac gtc tcc ctc tac gcg att aag gtg ttg aat       288
Leu Gly Val Ala Pro Asn Val Ser Leu Tyr Ala Ile Lys Val Leu Asn
                85                  90                  95 tca agc gga agc gga aca tac agc gca atc gtc agc gga att gag tgg       336
Ser Ser Gly Ser Gly Thr Tyr Ser Ala Ile Val Ser Gly Ile Glu Trp
            100                 105                 110 gcc aca caa aac ggc ctg gat gtc atc aac atg agc ctc ggc gga cca       384
Ala Thr Gln Asn Gly Leu Asp Val Ile Asn Met Ser Leu Gly Gly Pro
        115                 120                 125 tcc ggc tca act gcg ctg aaa cag gct gtg gat aaa gca tat gcc agc       432
Ser Gly Ser Thr Ala Leu Lys Gln Ala Val Asp Lys Ala Tyr Ala Ser
    130                 135                 140 gga att gtc gta gtg gca gca gcg ggg aac agc gga tct tcc ggc agc       480
Gly Ile Val Val Val Ala Ala Ala Gly Asn Ser Gly Ser Ser Gly Ser
145                 150                 155                 160 caa aac aca atc ggc tat ccg gca aaa tat gac tcc gtc atc gcc gtc       528
Gln Asn Thr Ile Gly Tyr Pro Ala Lys Tyr Asp Ser Val Ile Ala Val
                165                 170                 175 ggt gcg gtt gac agc aac aaa aac aga gct tca ttc tcc agc gtc ggc       576
Gly Ala Val Asp Ser Asn Lys Asn Arg Ala Ser Phe Ser Ser Val Gly
            180                 185                 190 tca gag ctt gaa gtc atg gct cct ggc gtc agc gta tac agc aca tat       624
Ser Glu Leu Glu Val Met Ala Pro Gly Val Ser Val Tyr Ser Thr Tyr
        195                 200                 205 cct tct aac acg tac aca tca ttg aac gga act tca atg gct tcg cct       672
Pro Ser Asn Thr Tyr Thr Ser Leu Asn Gly Thr Ser Met Ala Ser Pro
    210                 215                 220 cat gta gcg gga gca gca gcc ttg atc ttg tcg aaa tac cct acg ctt       720
His Val Ala Gly Ala Ala Ala Leu Ile Leu Ser Lys Tyr Pro Thr Leu
225                 230                 235                 240
```

```
tca gct tcc caa gtt cgc aac cgc ctc tca agc act gcg act aat ttg      768
Ser Ala Ser Gln Val Arg Asn Arg Leu Ser Ser Thr Ala Thr Asn Leu
                245                 250                 255 gga gat tcc ttc tac tac ggc aaa ggg ctg atc aat gta gaa gct gcc      816
Gly Asp Ser Phe Tyr Tyr Gly Lys Gly Leu Ile Asn Val Glu Ala Ala
            260                 265                 270 gct caa taa                                                          825
Ala Gln
```

<210> SEQ ID NO 2
<211> LENGTH: 274
<212> TYPE: PRT
<213> ORGANISM: Bacillus Licheniformis

<400> SEQUENCE: 2

```
Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
                20                  25                  30

Thr Gly Ile Ala Ser Ser His Thr Asp Leu Lys Val Val Gly Gly Ala
            35                  40                  45

Ser Phe Val Ser Gly Glu Ser Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
                100                 105                 110

Ala Thr Gln Asn Gly Leu Asp Val Ile Asn Met Ser Leu Gly Gly Pro
            115                 120                 125

Ser Gly Ser Thr Ala Leu Lys Gln Ala Val Asp Lys Ala Tyr Ala Ser
        130                 135                 140

Gly Ile Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190

Ser Glu Leu Glu Val Met Ala Pro Gly Val Ser Val Tyr Ser Thr Tyr
        195                 200                 205

Pro Ser Asn Thr Tyr Thr Ser Leu Asn Gly Thr Ser Met Ala Ser Pro
    210                 215                 220

His Val Ala Gly Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
                245                 250                 255

Gly Asp Ser Phe Tyr Tyr Gly Lys Gly Leu Ile Asn Val Glu Ala Ala
            260                 265                 270

Ala Gln
```

<210> SEQ ID NO 3
<211> LENGTH: 20
<212> TYPE: DNA
<213> ORGANISM: Artificial Sequence
<220> FEATURE:
<223> OTHER INFORMATION: Chemically - synthesized Primer PDE-2

-continued

```
<400> SEQUENCE: 3
agagcggcgg aaaagtggac                                              20

<210> SEQ ID NO 4
<211> LENGTH: 20
<212> TYPE: DNA
<213> ORGANISM: Artificial Sequence
<220> FEATURE:
<223> OTHER INFORMATION: Chemically-synthesized Primer PDE-5

<400> SEQUENCE: 4
cctgcgccag gagccatgac                                              20
```